US006438197B2

(12) United States Patent
Stierstorfer

(10) Patent No.: US 6,438,197 B2
(45) Date of Patent: Aug. 20, 2002

(54) X-RAY COMPUTED TOMOGRAPHY APPARATUS WITH CORRECTION FOR BEAM HARDENING

(75) Inventor: Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/902,385

(22) Filed: Jul. 10, 2001

(30) Foreign Application Priority Data

Jul. 24, 2000 (DE) .......................................... 100 35 984

(51) Int. Cl.[7] .................................................. A61B 6/03
(52) U.S. Cl. .............................. 378/8; 378/19; 378/901; 378/4
(58) Field of Search ............................ 378/4, 8, 15, 19, 378/901

(56) References Cited

U.S. PATENT DOCUMENTS 4,709,333 A 11/1987 Crawford
5,307,264 A * 4/1994 Waggener et al. ............ 378/14
6,324,240 B1 * 11/2001 Yan et al. ....................... 378/4

* cited by examiner

*Primary Examiner*—David V. Bruce
(74) *Attorney, Agent, or Firm*—Schiff Hardin & Waite

(57) ABSTRACT

In an X-ray computed tomography apparatus having a radiation filter, a patient attenuation value representative of the linear beam attenuation by a patient under examination is determined in an equation containing a correction function. The correction function is determined by first determining a set of reference overall attenuation values that, for a given different thicknesses of a reference material and different thicknesses of the radiation filter arrangement, represent the actual overall attenuation by the two materials. Then, an appertaining attenuation error value is determined for each reference overall attenuation value. Subsequently, a variable is defined changes in a direction transverse to straight lines of constant attenuation error values in a characteristic field of the attenuation error. Then, data about an error function dependent on the variable are determined, the error function representing the curve of the attenuation error along a reference curve placed into the attenuation error characteristic field.

12 Claims, 4 Drawing Sheets

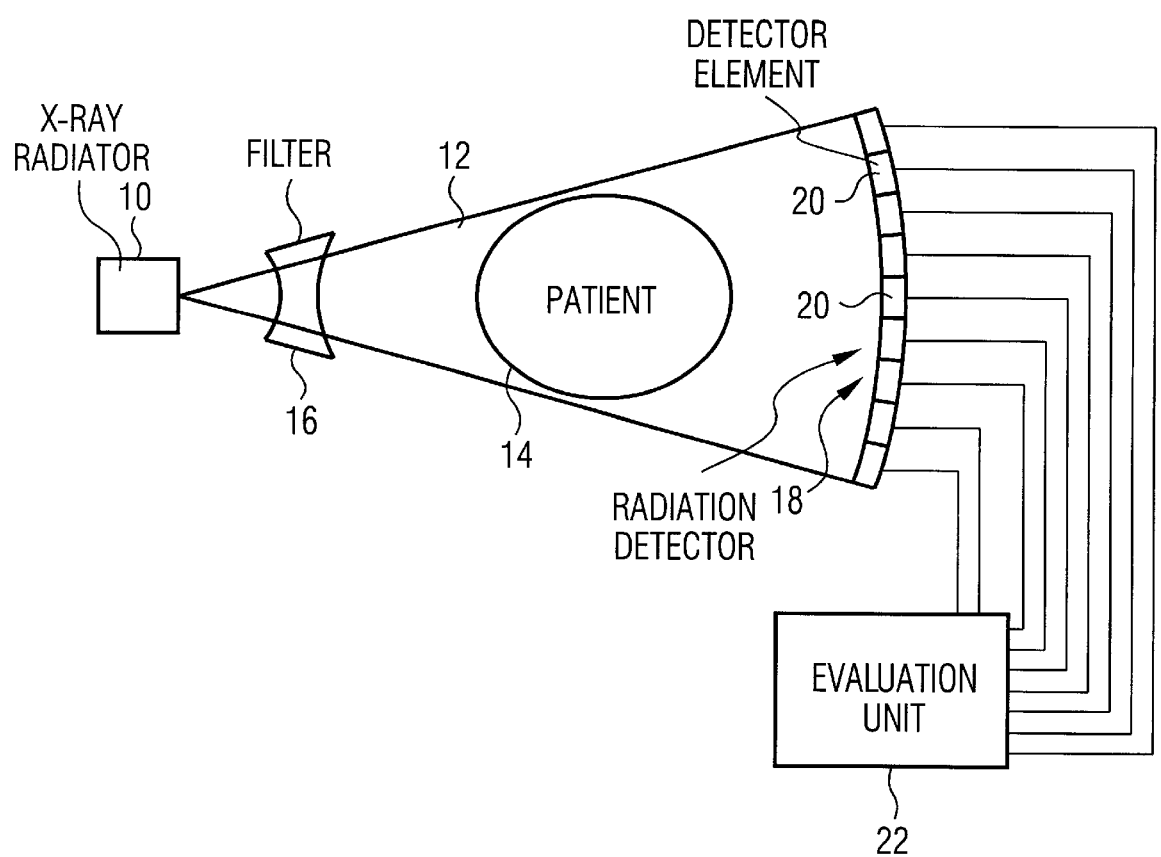

X-RAY COMPUTED TOMOGRAPHY APPARATUS WITH CORRECTION FOR BEAM HARDENING

BACKGROUND OF THE INVENTION

1. Field of the Invention

The present invention is directed to correcting beam hardening in an X-ray computed tomography apparatus.

2. Description of the Prior Art

As a consequence of the spectral dependency of the beam attenuation behavior in an irradiated object, a shift of the average or mean energy of the X-radiation emerging from a transirradiated body toward higher energy values occurs given polychromatic X-radiation. This effect is referred to as beam hardening. In computed tomography, beam hardening causes gray scale deviations in the reconstructed image of the body compared to the theoretical case of linear, spectrally independent beam attenuation. These gray scale deviations—or beam hardening artifacts—in the reconstructed image interfere with the diagnostic content of the image and can lead to misinterpretations in the worst case.

Numerous approaches are proposed in the literature for correcting image artifacts caused by beam hardening. For example, one approach disclosed in U.S. Pat. No. 4,709,333 is known as polynomial correction. Using an attenuation value obtained by measurement that indicates the actual beam attenuation of a body affected by beam hardening, a corrected attenuation value that is employed as the basis of the image reconstruction is calculated by inserting this attenuation value into a suitable polynomial identified in a calibration phase.

SUMMARY OF THE INVENTION

An object of the present invention is to provide a computed tomography apparatus which is operable to effectively correct for beam hardening.

This object is inventively achieved in an X-ray computed tomography apparatus having an X-ray radiator, a radiation filter arrangement arranged in the beam path of the X-rays emitted by the X-ray radiator, a detector arrangement that detects the X-rays that pass through a patient under examination and provides a set of measured intensity values for each slice projection, each of these measured intensity values being representative of the intensity of the detected X-rays in a respective projection sub-region of the slice projection, and has an electronic evaluation unit that determines an overall attenuation value for each of the measured intensity values that is representative of the actual overall attenuation of the X-rays in the respective projection sub-region effected by the radiation filter arrangement and the patient, and that determines a patient attenuation value corrected for beam hardening for each of the overall attenuation values that is representative of the theoretical, linear attenuation of the X-rays by the patient in the respective projection sub-region.

BRIEF DESCRIPTION OF THE DRAWINGS

FIG. 4 is a block diagram schematically illustrating the basic components of an X-ray computed tomography apparatus constructed and operating in accordance with the principles of the present invention.

DESCRIPTION OF THE PREFERRED EMBODIMENTS

Figure 1:
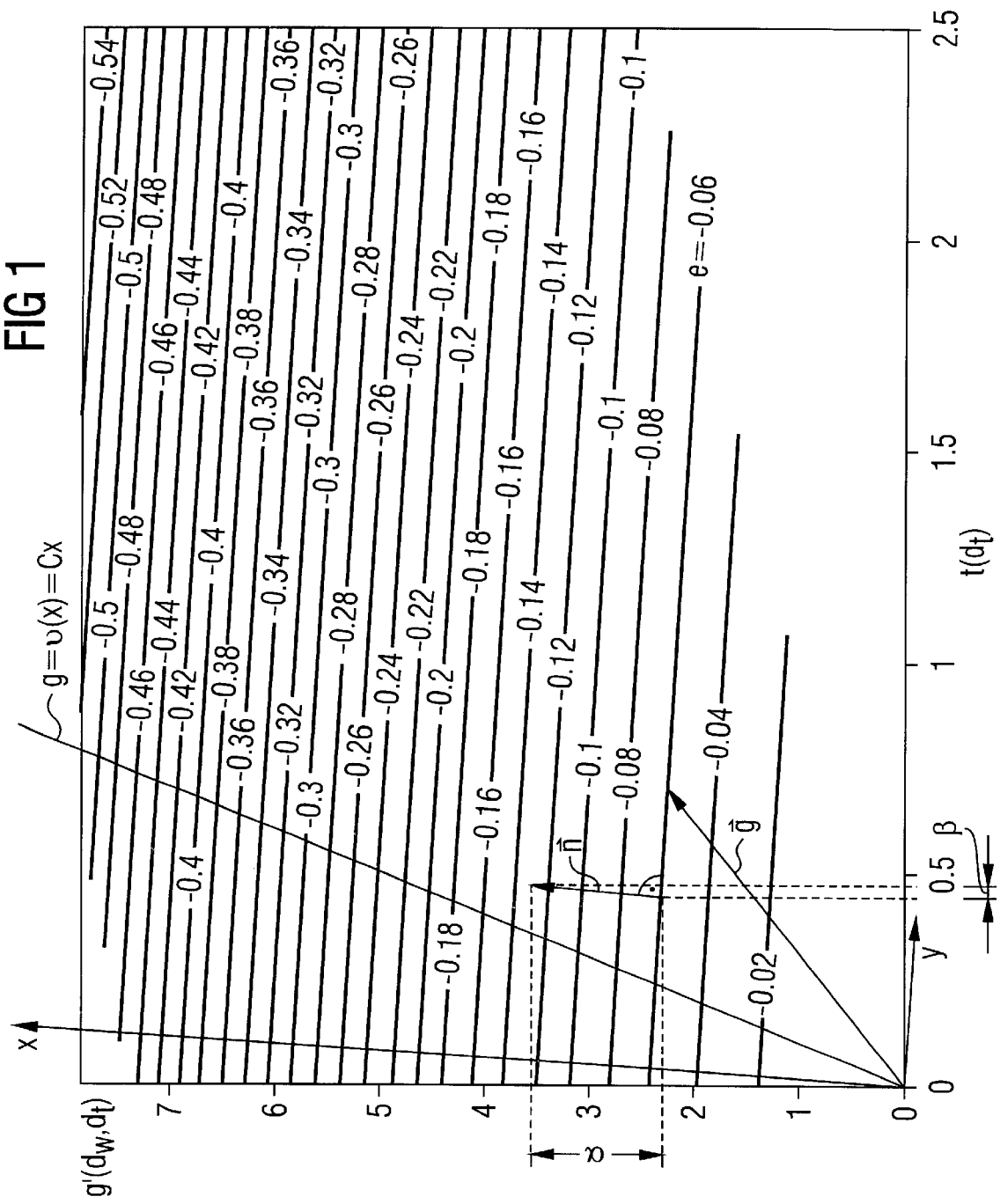
FIG. 1 shows an exemplary attenuation characteristics field in which a number of lines of constant attenuation error are entered, in accordance with the invention.

In accordance with the invention, data about a correction function $k(z)$ dependent on a variable z are stored in an evaluation unit, and the evaluation unit is configured for determining the respectively appertaining patient attenuation value for each overall attenuation value according to the following equation:

$$p = g - f - k(\alpha g + \beta f) \quad (1)$$

wherein p is the patient attenuation value to be respectively determined, g is the respective overall attenuation value, f is a filter attenuation value that is representative of the theoretical linear attenuation of the X-rays by the radiation filter arrangement in the respective projection sub-region, $k(\alpha g + \beta f)$ is the value of the correction function at the location $z = \alpha g + \beta f$, and $\alpha$ and $\beta$ are constants. The correction function $k(z)$ is determined according to the following method:

a) first, a set of reference overall attenuation values is determined for a combination of the material of the radiation filter arrangement and a reference material, the reference overall attenuation values being representative of the overall attenuation of the X-rays produced by this combination of materials for different thicknesses of the filter material and of the reference material, taking at least the beam hardening into consideration;

b) an appertaining attenuation error value is then determined for each of the reference overall attenuation values according to the following equation:

$$e(d_w, d_t) = g'(d_w, d_t) - w(d_w) - t(d_t) \quad (2),$$

wherein $e(d_w, d_t)$ is the attenuation error value given a thickness $d_w$ of the reference material and a thickness $d_t$ of the filter material, $g'(d_w, d_t)$ is the reference overall attenuation value given the thickness $d_w$ of the reference material and the thickness $d_t$ of the filter material, $w(d_w)$ is a first individual attenuation value that is representative of the theoretical linear attenuation of the X-radiation by the reference material given the thickness $d_w$ of the reference material, and $t(d_t)$ is a second individual attenuation values that is representative of the theoretical linear attenuation of the X-radiation by the filter material given the thickness $d_t$ of the filter material;

c) subsequently, the constants $\alpha$ and $\beta$ are defined such that the value of a variable x with $$x = \alpha g'(d_w, d_t) + \beta t(d_t) \quad (3)$$

changes in the direction transverse to lines of constant attenuation error in a $(g'(d_w, d_t), t(d_t))$ characteristics field of the attenuation error;

d) subsequently, information about an error function $u(x)$ dependent on the variable x are determined, said error function $u(x)$ representing the curve of the attenuation error along a reference curve $v(x)$ placed into the attenuation error characteristics field;

e) finally, the correction function $k(z)$ is determined according to the following equation:

$$k(z) = u(x=z) \quad (4).$$

In the inventive solution, a correct value for the linear patient attenuation p could be derived from Equation (1) when the correction value k is equal to the attenuation error between the overall attenuation g and the sum of the linear filter attenuation f and the linear patient attenuation p. For examination of a patient, however, the value of this attenuation is not known because of ignorance about the spatial distribution of the attenuation coefficient in the examined body slice. In the inventive solution, an attenuation error that is acquired in the course of an examination of, in particular, a homogeneous reference material having known attenuation behavior is therefore employed for the correction value k. It is expedient to select a reference material whose attenuation properties are similar to those of body tissue, for which reason water is preferably employed as the reference material. As used herein, the term 'patient' stands for arbitrary examination subjects.

In order to acquire information about this attenuation error, the attenuation behavior of the material combination of the reference material and a filter material employed in the radiation filter arrangement is determined in a calibration phase with a tandem arrangement of the reference material and the filter material employed in the radiation filter arrangement. This can ensue either by computer simulation but it is also possible to undertake concrete measurements in an experiment. Reference overall attenuation values are thereby determined for a number of different thicknesses of the filter material and for a number of different thicknesses of the reference material, the reference overall attenuation values respectively indicating the overall attenuation of the X-rays affected by beam hardening effected by the material combination of filter and reference material given the respective thicknesses of the two materials. It is self-evident that only the material thickness effective in the sense of a radiation attenuation is employed as the thickness of the filter or reference material, i.e. the material thickness in the direction of the beam path of the X-rays. A set of reference overall attenuation values g'($d_w$, $d_t$) is thus obtained that are dependent on the thickness $d_w$ of the reference material and on the thickness $d_t$ of the filter material and are respectively allocated to a pair combination of thickness $d_w$ of the reference material and thickness $d_t$ of the filter material. The attenuation error is then calculated according to Equation (2) from the difference between reference overall attenuation g'($d_w$, $d_t$) and the sum of linear attenuation w($d_w$) by the reference material and linear attenuation t($d_t$) by the filter material. The following applies to these two linear attenuations:

$$w(d_w) = \mu_w d_w \quad (5)$$

$$t(d_t) = \mu_t d_t \quad (6),$$

wherein $\mu_w$ is an attenuation coefficient of the reference material effective for linear attenuation and $\mu_t$ is the corresponding effective attenuation coefficient of the filter material.

It is theoretically possible, during use of the X-ray computed tomography apparatus, to determine the value of the attenuation error for the current value of the overall attenuation g in a projection sub-region and the appertaining, current value of the filter attenuation f, this attenuation error having been derived given identical values of the reference overall attenuation g' and the attenuation t by the filter material, and to utilize the attenuation error value e determined in this way as the correction value k for the respective projection sub-region. This, however, would require that the attenuation error value e be present in table form dependent on two variables, namely on the reference overall attenuation g' and the filter material attenuation t. In order to be sufficiently exact, such a table would have to contain attenuation error values for an extremely large number of (g', t)-value pairs. The realization outlay for this would be considerable.

With the inventive solution, by contrast, dependency of the attenuation error value e is reduced to dependency on a single variable. To this end, the variable x is introduced according to Equation (3), this being interpreted as the scalar product of a vector ($\alpha$, $\beta$) with a vector (g'($d_w$, $d_t$), t($d_t$)). The value of the variable x, accordingly, is a criterion for the length of the vector (g'($d_w$, $d_t$), t($d_t$)) in the direction of the vector ($\alpha$, $\beta$). In order to obtain an unambiguous allocation between the variable x and the attenuation error e, the vector ($\alpha$, $\beta$) is defined such that it is directed transverse to lines of constant value of the attenuation error e in a (g', t) characteristics field of the attenuation error e. This is equivalent to the amount that the variable x changes from one line of constant attenuation error value to the next.

FIG. 1 shows an exemplary (g', t) attenuation characteristics field into which a number of lines of constant attenuation error e are entered with a specification of the respective value of the attenuation error. It should be noted that, due to the definition of the attenuation error according to Equation (2), its value is always negative. The amount of the attenuation error also steadily increases toward higher values of g' and t. It can be seen from FIG. 1 that, to a very good approximation, the value of the attenuation error is constant on a family of parallel straight lines. This unanticipated perception favors the coordinate transformation according to Equation (3).

The vector ($\alpha$, $\beta$) under discussion is then defined such that it is essentially normal to the straight lines. The length of this normal vector in the direction of the g'-axis of the (g', t) characteristics field is thereby selected for the value of $\alpha$, whereas the length of the normal vector in the direction of the t-axis of the (g', t) characteristics field is selected for the value of $\beta$. For the sake of simplicity, $\alpha$=1 can thereby be applied. The variable x then has essentially the same value for each value pair (g', t) lying on one of the straight lines in the family of straight lines. This means that, in this case, the coordinate transformation according to the above Equation (3) enables an unambiguous allocation of each of the straight lines from the family of straight lines to an x-value and, consequently, enables an unambiguous allocation of an attenuation error value to each x-value. For illustration, a normal vector n to the straight line e=−0.06 is entered as an example in FIG. 1. Further, a vector q is entered that belongs to a value pair of g' and t lying on the straight line e=−0.06. It can be easily replicated that each vector directed onto the straight line e=−0.06 has an identical projection in the direction of the normal vector n and, thus, an identical x-value.

After the two variables g' and t have been reduced to the variable x by the coordinate transformation according to Equation (3), the relationship between the value of the attenuation error e and the value of the variable x must still be found. To this end, a reference curve v(x0 dependent on the variable x is defined and along which the profile of the attenuation error e is to be determined v(x) should be selected such that a separate function value v(x) is allocated to each value of x. Moreover, the reference curve v(x) should be placed such into the (g', t) characteristics field that it passes through a region of this characteristics field wherein a significant part of the pairs of overall attenuation value g and filter attenuation value f occurring given examination of a patient is anticipated. In particular, the reference curve v(x) should lie in the proximity of the most important value pairs of g and t. In the simplest case, the reference curve v(x) is defined as a straight line, i.e.

$$v(x) = Cx \quad (7),$$

wherein C is a constant. The value of this constant C will be selected dependent on the aforementioned demands made of the position of the reference curve v(x).

It is self-evident that, instead of a straight line, some other, arbitrary shape can be fundamentally selected for the reference curve v(x). When a rectangular x-y coordinate system is defined with $$y = -\beta g'(d_w, d_t) + \alpha t(d_t) \quad (8)$$

and when the reference curve is described by $$y = v(x) \quad (9),$$

then the following is generally valid for an error function u(x) that indicates the value of the attenuation error e along the reference curve v(x):

$$u(x) = e(g'(x, v(x), t(x, v(x)))) = \left( \frac{\alpha x - \beta v(x)}{\alpha^2 + \beta^2}, \frac{\beta x + \alpha v(x)}{\alpha^2 + \beta^2} \right). \quad (10)$$

In the above Equation (10), the first term in the argument of e indicates the coordinate value of the attenuation error along the g'-axis of the characteristics field according to FIG. 1, whereas the second term indicates the t-coordinate value. The error function u(x) can be modeled as look-up table. However, it is also conceivable to express the curve of the attenuation error e along the reference curve v(x) with the assistance of a mathematical equation. A polynomial approximation can lead to good results here. It has been shown that a polynomial of the fourth degree having the form $$u(x) = a_4 x^4 + a_3 x^3 + a_2 x^2 + a_1 x \quad (11)$$

often suffices in order to approximate the error curve along the reference curve v(x) with acceptable precision.

It is to be noted that, in practice, the lines of constant attenuation error e will usually not be exact straight lines and will also not proceed exactly parallel to one another. For this reason, a function value u(x=αg'+βt) that essentially corresponds to the exact value of the attenuation error e for the respective value pair (g', t) can in fact be obtained for value pairs of g' and t that lie on the reference curve v(x). For value pairs of g' and t that do not lie on the reference curve v(x), however, a function value u(x=αg'+βt) will be obtained that, under certain circumstances, deviates slightly from the actual value of the attenuation error for the appertaining value pair (g', t). The coincidence between the function value u(x) and the actual value of the attenuation error e is especially high in the proximity of that straight line of constant attenuation error e for which the normal vector n and, thus, the values of α and β were determined. It is therefore recommendable to determine the normal vector n for a straight line of constant attenuation error e that passes through the principal region of the value pairs of g and f to be anticipated in the examination of a patient. Given the characteristics field of FIG. 1, a beneficial selection would, for example, would be the straight line e=−0.2.

Figure 2:
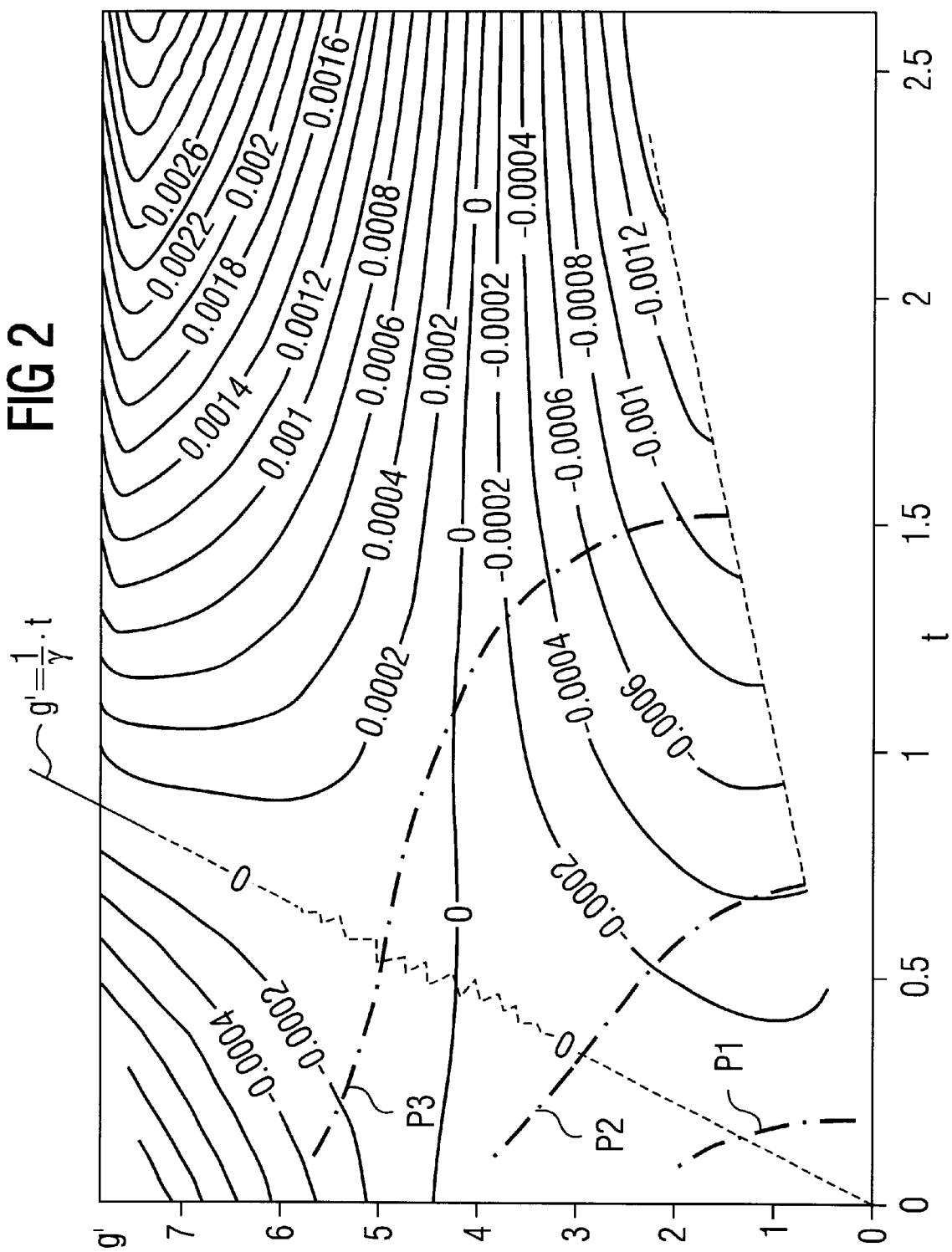
FIG. 2 shows a characteristics field wherein lines of constant residual error are entered, wherein the function $u(x)$ was implemented as a look-up table, in accordance with the invention.
Figure 3:
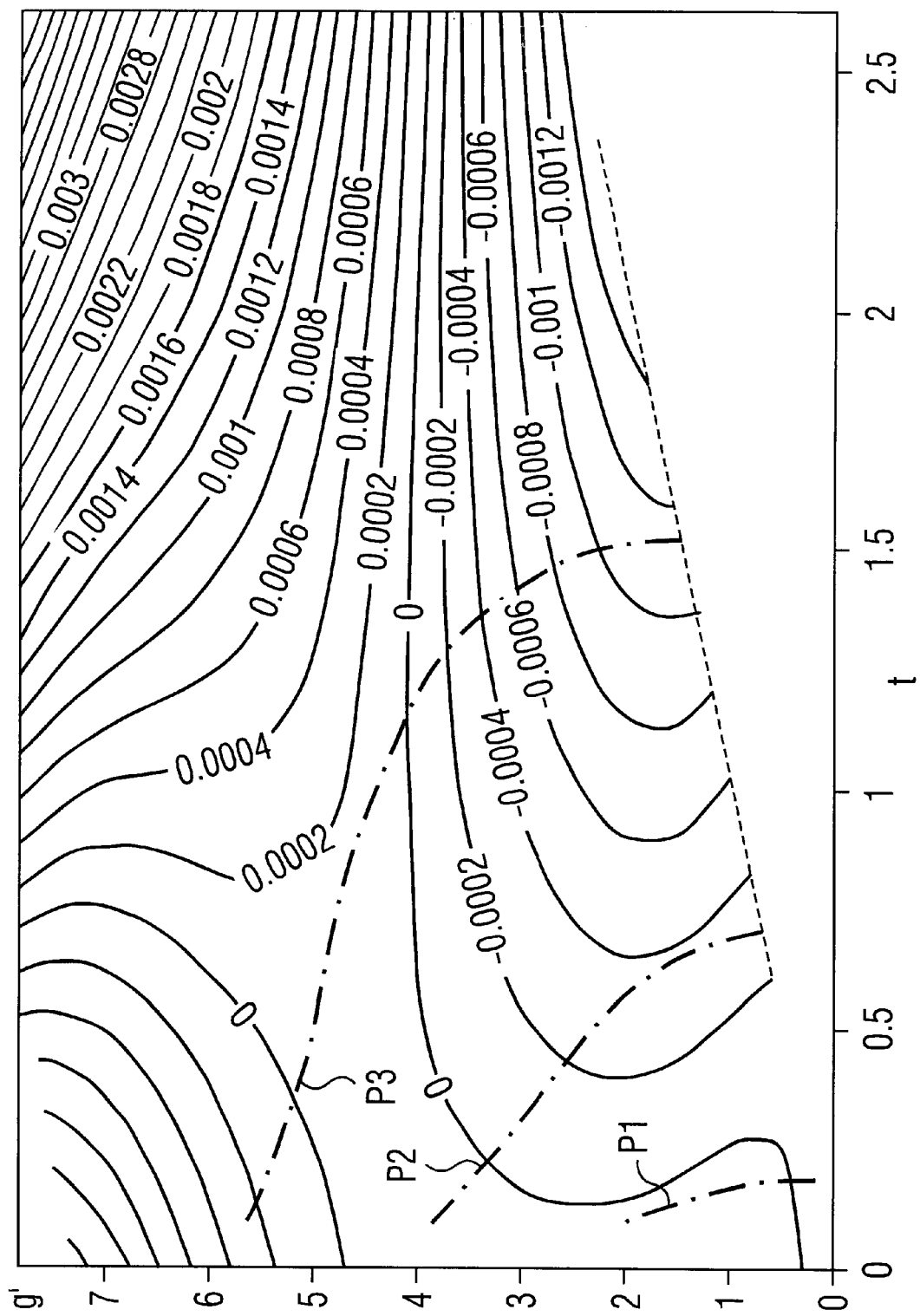
FIG. 3 shows a characteristics field wherein lines of constant residual error are entered, wherein the function $u(x)$ was implemented as a polynomial of the fourth degree table, in accordance with the invention.

FIGS. 2 and 3 shows (g', t) characteristics fields wherein lines of constant residual error are entered, with the residual error being defined from the difference between the function value u(x) determined for a respective value pair of g' and t and the actual value of the attenuation error e for this value pair (g', t) taken from the characteristics field of FIG. 1. FIG. 2 thereby shows an example wherein the function u(x) was implemented as look-up table, whereas the function u(x) in the example of FIG. 3 was implemented as polynomial of the fourth degree. One can see that the amount of the residual error is negligibly slight in broad regions of the characteristics fields in both instances. Particularly in FIG. 2, one can see that the residual error approximately disappears along a straight line g'=(1/γ)t (whereby γ is approximately 0.1) that was employed as reference curve for the determination of the profile of the attenuation error.

Points of value pairs (g', t) that were acquired from projections of three central water phantoms having diameters of 10, 20 or, respectively, 30 cm are also entered in FIGS. 2 and 3. The dot-dash line referenced P1 was thereby obtained given the water phantom with a 10 cm diameter, the dot-dash line referenced P2 was obtained given the water phantom with a 20 cm diameter and the dot-dash line referenced P3 was obtained given the water phantom with a 30 cm diameter. It can be clearly seen that the value pairs of g' and t obtained for all three water phantoms lie in a region of the characteristics field wherein the residual error is decidedly slight both given implementation of the error function u(x) as look-up table as well as given modeling of the error function u(x) by a polynomial function.

The results shown in FIGS. 1 through 3 were obtained given employment of water as reference material and Teflon® (polytetrafluoroethylene) as the filter material. It has been shown, however, that the lines of constant attenuation error e in the (g', t) characteristics field can also be approximately assumed as a family of straight lines parallel to one another given other filter materials, for instance aluminum, so that the procedure described up to now for determining the error function u(x) can also be applied given other filter materials. It is also not precluded that reference materials other than water be employed.

FIG. 4 schematically shows the fundamental structure of an X-ray computed tomography apparatus operating according to the invention. An X-ray radiator 10 that emits a fan-shaped X-ray beam 12 onto a patient 14. A form filter 16 arranged between the X-ray radiator 10 and the patient 14 attenuates the X-rays toward the edge regions of the ray fan 12 in order to produce a uniform radiation load on all transirradiated regions of the patient 14. A detector arrangement 18 arranged in the beam path behind the patient 14 detects the intensity of the X-rays that have passed through the patient 14. The detector arrangement 18 is composed of a number of detector elements 20 arranged next to one another in the direction of the fan angle of the ray fan 12 that cover respective projection sub-regions of the entire projection region represented by the ray fan 12. Each of the detector elements 20 supplies a measured intensity value indicating the radiation intensity in the respective projection subregion to an electronic evaluation unit 22. Using the received measured intensity values, the evaluation unit 22 calculates the initially described overall attenuation values g in a known way, these values g indicating the actual overall attenuation of the X-rays in the respective projection sub-region caused by the patient 14 and by the form filter 16. The values of the linear patient attenuation p required for the image reconstruction are then calculated by the evaluation unit 22 according to Equation (1). The value of the error function u(x=z) is utilized according to Equation (4) for the correction value k(z=αg+βf). The error function u(x) is stored for this purpose in the evaluation unit 22, as described above either in table form or in the form of an algorithm. It is self-evident that the error function u(x) was determined for the filter material of which the form filter 16 is composed.

In the case of a simulation of the reference overall attenuation values g'($d_w$, $d_t$), stray radiation effects also can be additionally simulated in addition to beam hardening effects. When the reference overall attenuation values g'($d_w$, $d_t$) are experimentally determined in the framework of a test series, such stray radiations effects, of course, enter into the measured values anyway.

Although modifications and changes maybe suggested by those skilled in the art, it is the intention of the inventor to embody within the patent warranted hereon all changes and modifications as reasonably and properly come within the scope of his contribution to the art.

I claim as my invention:

1. X-ray computed tomography apparatus comprising an X-ray radiator having a focus from which X-rays, in a beam path, are emitted, at least said focus being adapted for rotation around a subject for irradiating said subject with said X-rays from a number of different projections;

a radiation filter arrangement disposed in said beam path;

a detector arrangement that detects X-rays in said beam path that have passed through said subject and emits a set of measured intensity values for each projection, each of said measured intensity values being representative of the intensity of the detected X-rays in a respective projection sub-region of the projection; and an electronic evaluation unit that is programmed to determine an overall attenuation value g for each of the measured intensity values that is representative of an actual overall attenuation of the X-radiation in the respective projection sub-region effected by the radiation filter arrangement and the subject and that determines a patient attenuation value p corrected for beam hardening for each of the overall attenuation values g that is representative of a theoretical, linear attenuation of the X-rays by the subject in the respective projection sub-region, said evaluation unit having data about a correction function k(z) dependent on a variable z stored therein, and the evaluation unit being programmed to determine a respective patient attenuation value for each overall attenuation value according to the equation:

$$p = g - f - k(\alpha g + \beta f)$$

wherein p is the patient attenuation value to be respectively determined, g is the respective overall attenuation value, f is a filter attenuation value that is representative of a theoretical linear attenuation of the X-rays by the radiation filter arrangement in the respective projection sub-region, k($\alpha$g+$\beta$f) is the value of the correction function at the location z=$\alpha$g+$\beta$f, and $\alpha$ and $\beta$ are constants, and wherein the evaluation unit is programmed to determine correction function k(z) by:

determining a set of reference overall attenuation values for a combination of a material of the radiation filter arrangement and a reference material, said reference overall attenuation values being representative of the overall attenuation of the X-radiation effected by said combination for different thicknesses of the filter material and of the reference material, at least taking the beam hardening into consideration; determining an appertaining attenuation error value for each of the reference overall attenuation values according to the equation:

$$e(d_w, d_t) = g'(d_w, d_t) - w(d_w) - t(d_t)$$

wherein e($d_w$, $d_t$) is the attenuation error value given a thickness $d_w$ of the reference material and a thickness $d_t$ of the filter material, g'($d_w$, $d_t$) is the reference overall attenuation value given the thickness $d_w$ of the reference material and the thickness $d_t$ of the filter material, w($d_w$) is a first individual attenuation value that is representative of the theoretical linear attenuation of the X-radiation by the reference material given the thickness $d_w$ of the reference material, and t($d_t$) is a second individual attenuation values that is representative of the theoretical linear attenuation of the X-radiation by the filter material given the thickness $d_t$ of the filter material; defining the constants $\alpha$ and $\beta$ such that a value of a variable $$x = \alpha g'(d_w, d_t) + \beta t(d_t)$$

changes in a direction transverse to lines of constant attenuation error in an attention error characteristics field (g'($d_w$, $d_t$), t($d_t$)) determining data about an error function u(x) dependent on the variable x, said error function u(x) representing a curve of the attenuation error along a reference curve v(x) placed into the attenuation error characteristics field; and determining the correction function k(z) according to the equation:

$$k(z) = u(x=z).$$

2. An apparatus as claimed in claim 1 wherein the reference overall attenuation values (g') are determined by computer simulation.

3. An apparatus as claimed in claim 1, wherein the reference overall attenuation values (g') are determined by measurement.

4. An apparatus as claimed in claim 1 wherein said reference material is water.

5. An apparatus as claimed in claim 1 wherein said evaluation unit is programmed to define $\alpha$ and $\beta$ as coordinates of a vector (n) that is substantially normal to a line of constant attenuation error in the attenuation error characteristics field, whereby $\alpha$ is the coordinate of said vector along the g'($d_w$, $d_t$) axis of the characteristics field and $\beta$ is the coordinate of the vector (n) along the t($d_t$) axis of the characteristics field.

6. An apparatus as claimed in claim 1 wherein said evaluation unit is programmed to place the reference curve v(x) at least partially into a region of the attenuation error value characteristics field wherein a significant part of the pairs of overall attenuation value (g) and filter attenuation value (f) is anticipated in an examination of said subject.

7. An apparatus as claimed in claim 1 wherein said evaluation unit is programmed to select a straight line Cx as the reference curve v(x), whereby C is a constant.

8. An apparatus as claimed in claim 1 wherein said error function u(x) as a mathematical equation stored in the evaluation unit.

9. An apparatus as claimed in claim 8, wherein said evaluation unit is programmed to determine the error function u(x) by polynomial approximation.

10. An apparatus as claimed in claim 1 wherein the error function u(x) is determined in table form and is stored in the evaluation unit.

11. An apparatus as claimed in claim 1 wherein said filter material is polytetrafluoroethylene.

12. An apparatus as claimed in claim 1 wherein said filter material is aluminum.

* * * * *